United States Patent
Okaya et al.

(10) Patent No.: US 11,181,465 B2
(45) Date of Patent: Nov. 23, 2021

(54) DEVICE FOR EVALUATING PARTICLES IN LIQUID AND METHOD FOR OPERATING SAME

(71) Applicant: Toray Industries, Inc., Tokyo (JP)

(72) Inventors: Shinji Okaya, Otsu (JP); Kyoya Takemoto, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 16/966,078

(22) PCT Filed: Jan. 18, 2019

(86) PCT No.: PCT/JP2019/001557
§ 371 (c)(1),
(2) Date: Jul. 30, 2020

(87) PCT Pub. No.: WO2019/150997
PCT Pub. Date: Aug. 8, 2019

(65) Prior Publication Data
US 2020/0363314 A1 Nov. 19, 2020

(30) Foreign Application Priority Data
Feb. 1, 2018 (JP) .............................. JP2018-016114

(51) Int. Cl.
*H04N 7/18* (2006.01)
*G01N 15/14* (2006.01)

(52) U.S. Cl.
CPC ............ *G01N 15/1436* (2013.01); *H04N 7/18* (2013.01)

(58) Field of Classification Search
CPC .............................. H04N 7/18; G01N 15/1436
(Continued)

(56) References Cited

U.S. PATENT DOCUMENTS

| 4,338,024 A | 7/1982 | Bolz et al. |
| 4,647,540 A | 3/1987 | Ozawa et al. |

(Continued)

FOREIGN PATENT DOCUMENTS

| JP | 57500995 A | 6/1982 |
| JP | 0353907 B2 | 8/1991 |

(Continued)

OTHER PUBLICATIONS

International Search Report and Written Opinion for International Application No. PCT/JP2019/001557, dated Mar. 5, 2019, 6 pages.

(Continued)

*Primary Examiner* — Nguyen T Truong
(74) *Attorney, Agent, or Firm* — RatnerPrestia

(57) ABSTRACT

The present invention provides a device for evaluating particles in a liquid, which is provided with: a main body member that has a first opening part and a second opening part, which face each other, and an internal hollow part; a first flow path and a second flow path, which are connected to the main body member and are in communication with the hollow part; a first drive member and a second drive member, which are arranged within the hollow part so as to face each other and which are slidable within the hollow part; a drive means which drives the first drive member and/or the second drive member in the facing direction within the hollow part; a liquid supply means which introduces a liquid containing particles into the hollow part through the first flow path; and an imaging means which captures an image of particles within the hollow part through the first opening part or the second opening part. This device for evaluating particles in a liquid is configured such that in cases where the first drive member and the second drive member are observed from the facing direction, the first drive member and the second drive member have portions (Continued)

that are wider than the first flow path and the second flow path.

6 Claims, 4 Drawing Sheets

(58) Field of Classification Search
 USPC ............................................................ 348/143
 See application file for complete search history.

(56) References Cited

U.S. PATENT DOCUMENTS

| | | |
|---|---|---|
| 2002/0118354 A1 | 8/2002 | Berndt |
| 2004/0048330 A1 | 3/2004 | Bittner |
| 2010/0315501 A1 | 12/2010 | Ludwig |
| 2011/0311996 A1 | 12/2011 | Friedberger et al. |
| 2013/0199270 A1 | 8/2013 | Singh et al. |
| 2014/0303931 A1 | 10/2014 | Suzuki |
| 2014/0367315 A1 | 12/2014 | Gluckstad |
| 2019/0080881 A1* | 3/2019 | Huang .............. H01J 37/32807 |

FOREIGN PATENT DOCUMENTS

| | | |
|---|---|---|
| JP | 2002323438 A | 11/2002 |
| JP | 2004503223 A | 2/2004 |
| JP | 2015503736 A | 2/2015 |
| TW | 201211534 A | 3/2012 |
| TW | I565937 B | 1/2017 |
| TW | I565937 B | 1/2017 |

OTHER PUBLICATIONS

Taiwan Office Action for Taiwan Application No. 108102425, dated Jul. 22, 2021 with translation, 9 pages.

* cited by examiner

[Fig. 1]
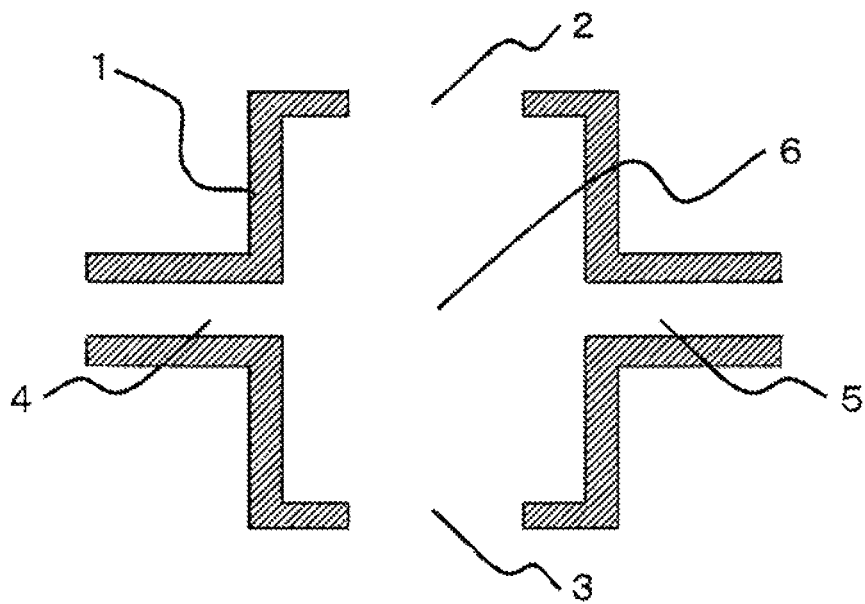
[Fig. 2]
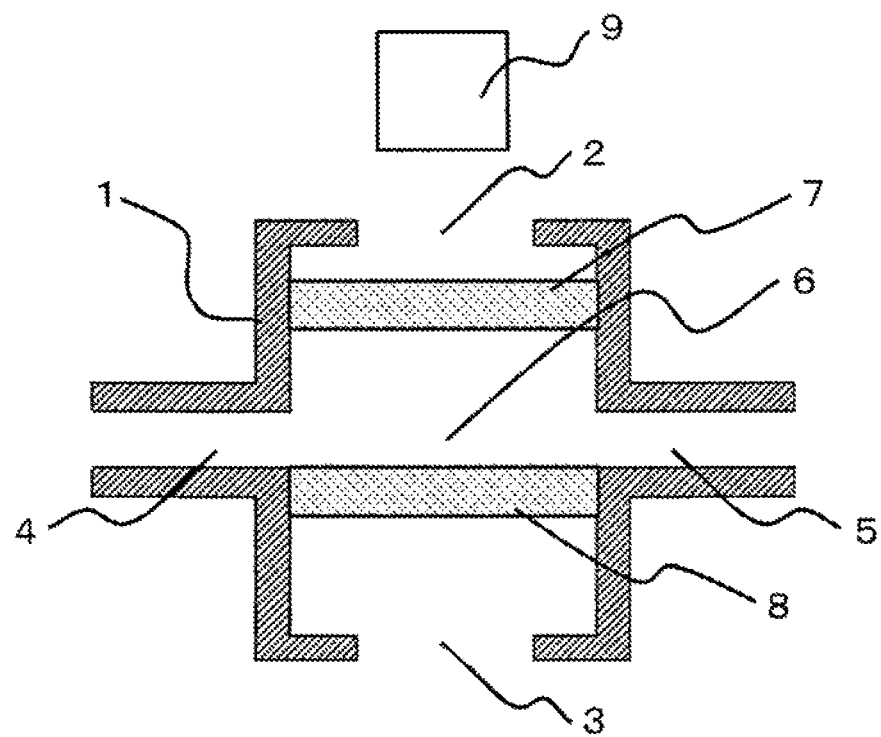

[Fig. 3]
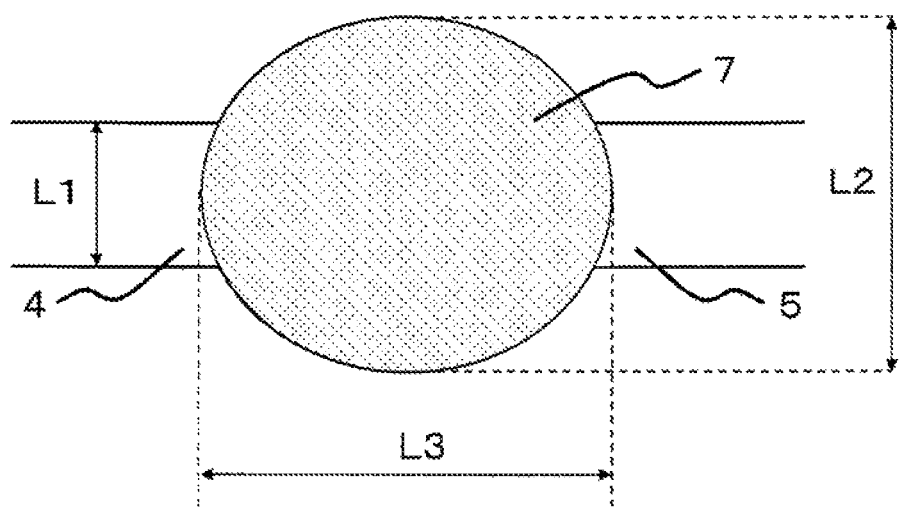

[Fig. 4a]
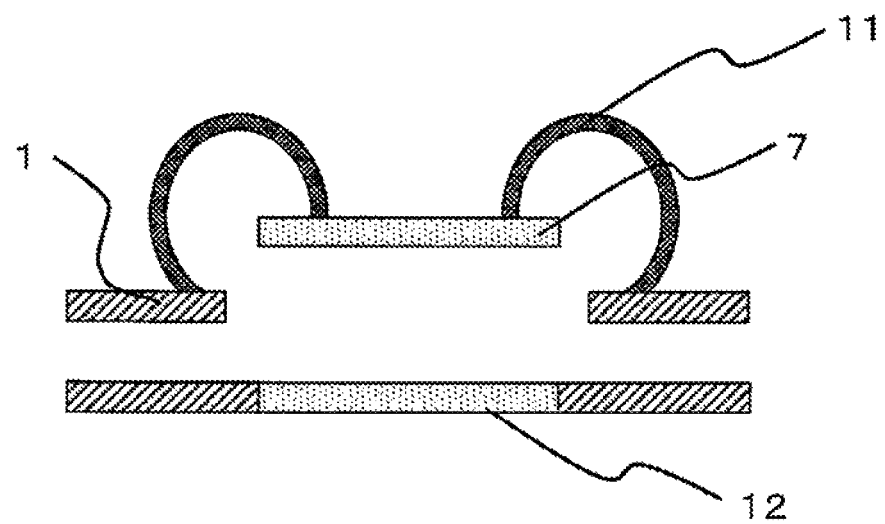
[Fig. 4b]
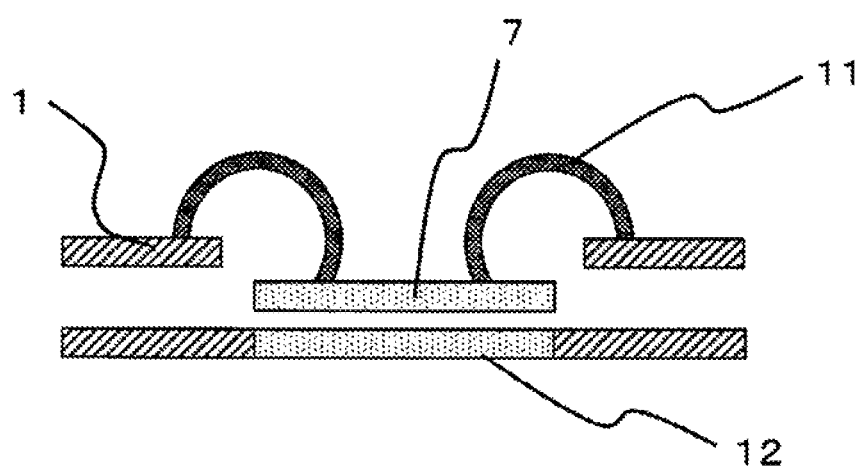

[Fig. 5a]
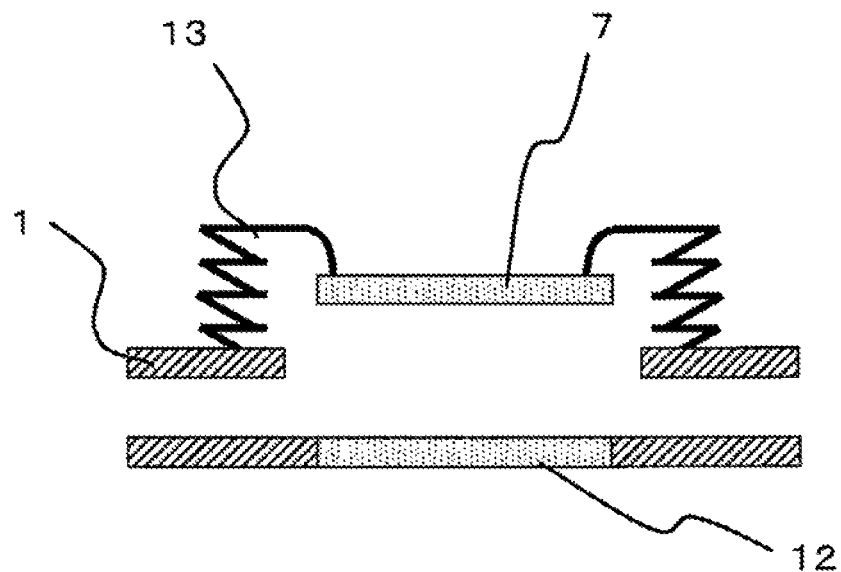
[Fig. 5b]
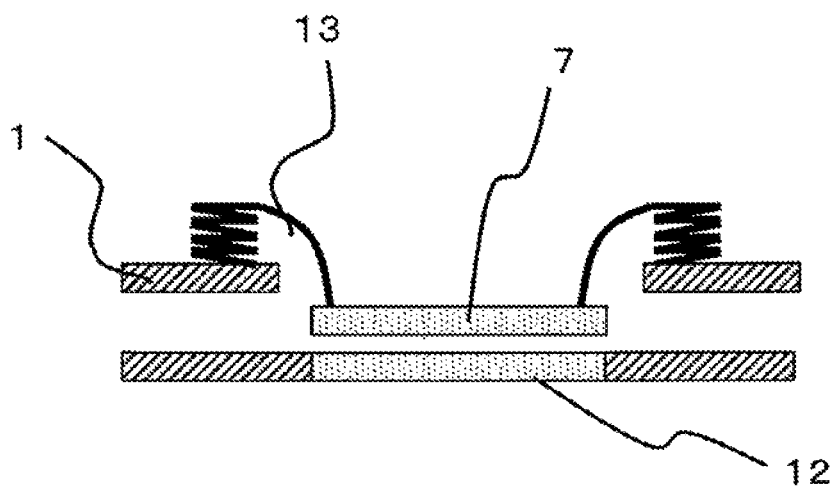

DEVICE FOR EVALUATING PARTICLES IN LIQUID AND METHOD FOR OPERATING SAME

CROSS REFERENCE TO RELATED APPLICATIONS

This is the U.S. National Phase application of PCT/JP2019/001557, filed Jan. 18, 2019, which claims priority to Japanese Patent Application No. 2018-016114, filed Feb. 1, 2018, the disclosures of each of these applications being incorporated herein by reference in their entireties for all purposes.

FIELD OF THE INVENTION

The present invention relates to a device for evaluating particles in a liquid and a method for operating the device.

BACKGROUND OF THE INVENTION

A technique of fixing a part of a test liquid containing particles to a specific region while adjusting a gap between two transparent glass in accordance with a size of the particles in the liquid is known as means for automatically observing particles in a liquid such as microorganisms in a test liquid (Patent Literatures 1 and 2).

PATENT LITERATURE

Patent Literature 1: JP-B-H3-53907
Patent Literature 2: JP-A-2004-503223

SUMMARY OF THE INVENTION

However, in the technique in the background art (Patent Literatures 1 and 2), drive members such as transparent glasses are moved up and down, and particles in the liquid to be observed are crushed and adhered to a drive member. It has been considered a problem that the adhered substances not only hinder automatic observation, but also requires a great burden to remove them.

Therefore, an object of the present invention is to provide a device for evaluating particles in a liquid, which can greatly prevent adhesion of particles in a liquid to a drive member or the like while observing the particles in a test liquid, with a suitable gap by driving the drive member in a opposite direction (up-down driving), and a method for operating the device.

In order to achieve the above object, one embodiment of the present invention includes a device for evaluating particles in a liquid of the present invention including:
a main body member including a first opening part and a second opening part facing each other, and an hollow part inside thereof;
a first flow channel and a second flow channel connected to the main body member and communicating with the hollow part;
a first drive member and a second drive member which are provided in the hollow part so as to face each other and being slidable within the hollow part;
a drive means for driving the first drive member and/or the second drive member in a facing direction within the hollow part;
a liquid feeding means for introducing a liquid containing particles into the hollow part through the first flow channel; and
an imaging means for capturing an image of particles within the hollow part through the first opening part or the second opening part,
in which when observing the first drive member and the second drive member from the facing direction, the first drive member and the second drive member include portions wider than the first flow channel and the second flow channel.

One embodiment of the present invention include a method for operating the device for evaluating particles in a liquid including driving the first drive member and/or the second drive member such that a width between the first drive member and the second drive member in the facing direction is 0.01 mm or more and less than 0.05 mm during observation, and is 0.5 mm or more at times other than the observation.

The device for evaluating particles in a liquid of the present invention, and the method for operating the device enable to observe the particles in a liquid contained in a test liquid in a suitable gap by driving a first drive member and a second drive member in a facing direction (up-down driving), and further enable to greatly prevent the particles in a liquid from adhesion to a drive member or the like. Thus, the accuracy of observation results can be improved and the burden of device maintenance can be greatly reduced.

BRIEF DESCRIPTION OF DRAWINGS

FIG. 1 is a schematic diagram of a cross section of a main body member of the device for evaluating particles in a liquid according to a first embodiment of the present invention.

FIG. 2 is a schematic diagram of a cross section of the device for evaluating particles in a liquid according to the first embodiment of the present invention.

FIG. 3 is a schematic diagram of a first drive member when observed from a facing direction with a second drive member.

FIG. 4a is a schematic diagram of a cross section of the device for evaluating particles in a liquid according to a second embodiment of the present invention.

FIG. 4b is a schematic diagram of a cross section of the device for evaluating particles in a liquid according to the second embodiment of the present invention.

FIG. 5a is a schematic diagram of a cross section of the device for evaluating particles in a liquid according to a third embodiment of the present invention.

FIG. 5b is a schematic diagram of a cross section of the device for evaluating particles in a liquid according to the third embodiment of the present invention.

DETAILED DESCRIPTION OF EMBODIMENTS OF THE INVENTION

Preferred embodiments of the present invention will be described below with reference to the drawings.

First Embodiment

The device for evaluating particles in a liquid according to an embodiment of the present invention includes:
a main body member including a first opening part and a second opening part facing each other, and a hollow part inside of the body member;

a first flow channel and a second flow channel connected to the main body member and communicating with the hollow part;

a first drive member and a second drive member provided in the hollow part so as to face each other and being slidable within the hollow part;

a drive means for driving the first drive member and/or the second drive member in a facing direction within the hollow part;

a liquid feeding means for introducing a liquid containing particles into the hollow part through the first flow channel; and an imaging means for capturing an image of particles within the hollow part through the first opening part or the second opening part, in which when observing the first drive member and the second drive member from the facing direction, the first drive member and the second drive member include portions wider than the first flow channel and the second flow channel.

In the device for evaluating particles in a liquid according to the embodiment of the present invention, it is preferable that the first opening part and the second opening part face each other and communicate with the hollow part.

The device for evaluating particles in a liquid according to the embodiment of the present invention includes: a main body member including a first opening part and a second opening part facing each other and communicating with each other to form a hollow part, and a first flow channel and a second flow channel respectively communicating with the hollow part; a first drive member and a second drive member respectively fitted or loosely fitted to the hollow part; a drive means for driving the first drive member and/or the second drive member in a facing direction within the hollow part; a liquid feeding means for introducing a liquid containing particles into the hollow part through the first flow channel; and an imaging means for capturing an image of particles within the hollow part. When the first drive member and the second drive member are observed from the facing direction, the first drive member and the second drive member include portions wider than the first flow channel and the second flow channel.

The device for evaluating particles in a liquid according to the embodiment of the present invention may include a main body member including a first opening part and a second opening part facing each other and communicating with each other to form a hollow part, and a first flow channel and a second flow channel respectively communicating with the hollow part.

FIG. 1 is a schematic diagram of a cross section of a main body member of a device for evaluating particles in a liquid according to a first embodiment of the present invention. In the cross-sectional diagram of FIG. 1, a main body member 1 includes a first opening part 2 and a second opening part 3, which face each other, at one end of the main body member 1 and the other end thereof (up-down direction).

The first opening part 2 and the second opening part 3 have the same width in the main body member 1 of FIG. 1, however, for example, widths of the first opening part 2 and the second opening part 3 may be different, or opening shapes thereof may be different.

The main body member includes a first opening part and a second opening part facing each other, and a hollow part inside of the body member.

The main body member may have a tubular shape, a substantially cylindrical shape, or a polygonal tubular shape.

In addition, the first opening part may be provided at one end, and the second opening part may be provided at the other end.

The first opening part 2 and the second opening part 3 may communicate with each other to form a hollow part 6. In the device for evaluating particles in a liquid according to the embodiment of the present invention, a test liquid present in the hollow part 6 can be observed and evaluated through the first opening part 2 or the second opening part 3.

In the main body member 1 of FIG. 1, the hollow part has a uniform width as a whole from the first opening part 2 to the second opening part 3, however, the shape of the hollow part is not particularly limited. For example, the hollow part may have a variation in the width of the hollow part (swelling, constrictions, etc.), or may be curved.

In the cross-sectional diagram of FIG. 1, the main body member 1 includes a first flow channel 4 and a second flow channel 5 in side surfaces (left-right direction) of the main body member 1.

In FIG. 1, the first flow channel 4 and the second flow channel 5 have the same width and the same length in a width (up-down in FIG. 1) direction and a longitudinal (left-right in the figure) direction respectively, however, for example, the widths of the first flow channel 4 and the second flow channel 5 may be different, or shapes thereof may be different. In FIG. 1, the first flow channel 4 and the second flow channel 5 are provided at the same position in the length (up-down in FIG. 1) direction of the main body member 1 so as to face each other, and these flow channels may be provided at different positions.

The first flow channel 4 and the second flow channel 5 are connected to the main body member 1 separately and communicate with the hollow part 6.

Materials for forming the main body member are not particularly limited as long as they are not corroded by the test liquid, and examples thereof include metal such as stainless steel and aluminum.

The device for evaluating particles in a liquid according to the embodiment of the present invention requires a first drive member and a second drive member which are provided within the hollow part so as to face each other and which are slidable within the hollow part. In addition, the device for evaluating particles in a liquid of the present invention requires a drive means which drives the first drive member and/or the second drive member in a facing direction within the hollow part.

FIG. 2 is a schematic diagram of a cross section of the device for evaluating particles in a liquid according to the first embodiment of the present invention. The first drive member and the second drive member may be fitted or loosely fitted to the hollow part respectively. In the cross-sectional diagram of FIG. 2, a first drive member 7 and a second drive member 8 are fitted to the hollow part 6 of the main body member 1 respectively, and are in a state in which they can be driven by the drive means (not shown) while facing each other in the length (up-down in the figure) direction of the main body member 1.

Here, "fitted" means that the first drive member and the second drive member are respectively fitted to the hollow part so that the hollow part is in a liquid-tight state.

The first drive member and/or the second drive member may be in a state where the hollow part is not liquid-tight, that is, may be "loosely fitted".

Both of the first drive member and the second drive member may be driven within the hollow part, or only one of the first drive member and the second drive member may be driven within the hollow part.

In the latter case, the drive member on a non-driving side may be fixed by an adhesive or the like such that the first opening part or the second opening part, or a part of the hollow part is closed. Alternatively, a portion corresponding to the drive member on the non-driving side may be integrally molded together with the main body member. In these cases, with no strict interpretation, if it is assumed that the fixed drive member or the portion corresponding to the drive member does not exist, the first opening part and the second opening part can be regarded as parts which are in communication with each other to form a hollow part.

The first drive member and/or the second drive member may be driven not only within the hollow part but also from the inside of the hollow part to the outside of the hollow part.

In the device for evaluating particles in a liquid according to the embodiment of the present invention, a test liquid present in a partial region of the hollow part sandwiched by the first drive member and the second drive member is imaged and evaluated through the first drive member or the second drive member. Therefore, at least a part of the first drive member or the second drive member is preferably transparent or translucent. On the other hand, both of the drive members may include a transparent portion, or the entire drive member may be molded so as to be transparent.

Examples of a material for forming the transparent portion of the drive member include glass, an acrylic resin, and a polycarbonate resin. Examples of a material for forming a portion other than the transparent portion of the drive member include metal such as stainless steel and aluminum.

The device for evaluating particles in a liquid according to the embodiment of the present invention requires a liquid feeding means (not shown) which introduces a liquid containing particles into the hollow part through the first flow channel. In addition, the device for evaluating particles in a liquid according to the embodiment of the present invention requires an imaging means which captures an image of the particles in a liquid within the hollow part.

The liquid feeding means can introduce a liquid containing particles, that is, a test liquid, into the partial region of the hollow part sandwiched by the first drive member and the second drive member through the first flow channel. Then the imaging means can capture an image of the test liquid present in the partial region of the hollow part sandwiched by the first drive member and the second drive member and evaluate it. For example, the test liquid can be imaged and evaluated by an imaging means 9 through the first drive member 7 or the second drive member 8 in FIG. 2.

Examples of the liquid feeding means include a turbo (non-positive displacement) type pump or a positive displacement pump.

Examples of the imaging means include a camera including an element typified by a CCD or a CMOS, and it is preferable to properly use element sensitivity such as color or monochrome or UV or IR depending on an evaluation object.

The test liquid introduced to the partial region of the hollow part through the first flow channel is discharged to the outside of the hollow part through the second flow channel. Although a test liquid may be continuously introduced into a partial region of the hollow part, a test liquid within the partial region of the hollow part is retained temporarily to be imaged and evaluated in this state, by stopping a liquid flow of a test liquid into the first flow channel and/or the second flow channel by providing a closing means in the first flow channel and/or the second flow channel, thereby.

In the device for evaluating particles in a liquid according to the embodiment of the present invention, when the first drive member and the second drive member are observed from a facing direction, the first drive member and the second drive member are required to include a portion that is wider than the first flow channel and the second flow channel.

FIG. 3 is a schematic diagram of a case where the first drive member 7 is observed from a facing direction with the second drive member 8. When each of the first flow channel 4 and the second flow channel 5 has a constant with of L1, the first drive member 7 includes a portion having a width (a maximum width of L2) larger than the width L1 of the first flow channel 4 and the second flow channel 5. When the second drive member 8 (not shown in FIG. 3) is observed from a direction opposite to that of FIG. 3, the second drive member 8 includes a portion having a width larger than the width L1 of the first flow channel 4 and the second flow channel 5.

In a case where the first drive member 7 or the second drive member 8 in FIG. 3 does not have a portion having a width larger than the width L1 of the first flow channel 4 and the second flow channel 5, that is, in a case where the maximum width L2 of the first drive member 7 or the second drive member 8 is equal to or smaller than L1, when particles in a liquid having the same diameter as L1 are introduced into the hollow part and retained therein, the particles in a liquid are crushed by driving the first drive member 7 and/or the second drive member 8 in the facing direction (up-down driving). In that case, the crushed particles in a liquid lose their escape in the width direction of the first drive member 7 and the second drive member 8. Then, the crushed particles in a liquid are stretched without a gap in a direction of a length L3 of the first drive member 7 and the second drive member 8, and if pressure is further applied to the particles in a liquid, the probability that the particles in a liquid are adhered to the first drive member 7 and the second drive member 8 becomes higher.

On the other hand, as shown in FIG. 3, in a case where the first drive member 7 or the second drive member 8 has a portion having a width larger than the widths L1 of the first flow channel 4 and the second flow channel 5, even when particles in a liquid having the same diameter as L1 are introduced into the hollow part and retained therein, the particles in a liquid, which are crushed by driving the first drive member 7 and/or the second drive member 8 in the facing direction (up-down driving), can be stretched not only in a length direction but also in the width direction of the first drive member 7 and the second drive member 8, and the probability of stretching between the two drive members without a gap is significantly reduced. Therefore, the probability that the particles in a liquid adhere to the first drive member 7 and the second drive member 8 can be significantly reduced.

When the lengths L3 of the first drive member 7 and the second drive member 8 is excessively short, it is more likely that the particles in a liquid is retained in the hollow part 6, or that cleaning of the hollow part 6 is insufficient. On the other hand, when L3 is excessively long, clogging of the particles in a liquid introduced into the hollow part 6 is more likely. Therefore, L3 is preferably similar in length to L2, and further, shapes of the first drive member 7 and the second drive member 8 when observing the first drive member 7 and the second drive member 8 in the facing directions of each other are more preferably substantially circular or polygonal, and are still more preferably substantially circular, from the viewpoint of preventing the retained particles in a liquid from being caught.

The width between the first drive member and the second drive member in the facing direction may be appropriately determined depending on an average size of the particles in a liquid or a depth of field of the imaging means provided in the device for evaluating particles in a liquid according to the embodiment of the present invention, and during the observation of the particles in a liquid, the width is preferably 0.01 mm or more when the particles in a liquid is activated sludge, from the viewpoint of imaging resolution and position repeatability of a drive member. In addition, the width between the first drive member and the second drive member in the facing direction during the observation of the particles in a liquid is preferably less than 0.05 mm from the viewpoint of preventing the particles in a liquid from being misrecognized due to overlapping in the up-down direction.

On the other hand, the width between the first drive member and the second drive member is preferably 0.5 mm or more in order to prevent clogging of the hollow part, at times other than the observation of the particles in a liquid. The width between the first drive member and the second drive member at times other than the observation of the particles in a liquid is preferably 1 mm or less in order to avoid an increase in the observation time due to the drive time. At times other than the observation of the particles in a liquid, the particles in a liquid adhered to the first drive member and the second drive member are likely to be released, thus, the introduction of a test liquid and the driving of the first drive member and the second drive member in the facing direction (up-down driving) are preferably repeated intermittently.

In the method for operating the device for evaluating particles in a liquid according to the embodiment of the present invention, the first drive member and/or the second drive member are driven such that the width between the first drive member and the second drive member in the facing direction is 0.01 mm or more and less than 0.05 mm during the observation, and is 0.5 mm or more at times other than the observation.

The first drive member and/or the second drive member are/is driven in the facing direction preferably at a speed of 5 mm/s or less in order to reduce the chance of destruction of the drive member or the like while making evaluation time including the imaging appropriate. In addition, from the viewpoint of work efficiency, it is preferable to set the speed to be 0.5 mm/s or more.

Second Embodiment

FIGS. 4a and 4b are schematic diagrams of a cross section of a body member of a device for evaluating particles in a liquid according to the second embodiment of the present invention. The device for evaluating particles in a liquid according to the second embodiment of the present invention includes a coupling member, which is attached to the main body member and the first drive member and maintains a liquid-tight state between the main body member and the first drive member, in addition to the constituent elements of the device for evaluating particles in a liquid according to the first embodiment of the present invention.

In the cross-sectional diagrams of FIGS. 4a and 4b, the first drive member 7 is loosely fitted to the hollow part 6 of the main body member 1, and the second drive member 12 is fitted to the hollow part 6 of the main body member 1.

Here, the first drive member 7 is in a state in which it can be driven by a drive means (not shown) while facing with the second drive member 12 in the length direction of the main body member 1 (up-down direction in the figure). On the other hand, the second drive member 12 is configured not to be driven, and is fixed by adhesion so as to close the second opening part. As described above, the second drive member that is not driven may be integrally molded with the main body member.

In the cross-sectional diagrams of FIGS. 4a and 4b, the first drive member 7 loosely fitted to the hollow part 6 of the main body member 1 is configured to be driven not only within the hollow part 6 but also from the inside of the hollow part 6 to the outside of the hollow part 6. In such a configuration, the device for evaluating particles in a liquid according to the second embodiment of the present invention includes a coupling member 11 as shown in FIGS. 4a and 4b so as to maintain a liquid-tight state between the main body member and the first drive member. The coupling member 11 is attached to each of the main body member 1 and the first drive member 7.

A shape of the coupling member may be appropriately determined depending on a material of the coupling member, a drive range of the first drive member, or the like. The coupling member may be an elastic member, and examples of the material of the coupling member include a resin, a rubber, or an elastomer that can be expanded and contracted while having a constant tear strength.

Examples of a method for attaching the coupling member 11 to each of the main body member and the first drive member include fixing by adhesion or the like.

Third Embodiment

FIGS. 5a and 5b are schematic diagrams of a cross section of a main body member of a device for evaluating particles in a liquid according to the third embodiment of the present invention. In the device for evaluating particles in a liquid according to the third embodiment of the present invention, a coupling member corresponding to that in the device for evaluating particles in a liquid according to the second embodiment of the present invention has a bellows structure.

In the cross-sectional diagram of FIG. 5a, the coupling member 13 has a bellows structure. When a coupling member 13 has a bellows structure, the coupling member 13 can be expanded and contracted without being largely deviated in a lateral direction (left and right) even when the first drive member 7 is driven in the facing direction (up-down driving) as shown in FIG. 5b, and the evaluation of the particles in a liquid can be performed more stably.

INDUSTRIAL APPLICABILITY

The present invention can be suitably used for evaluating a state of particles in a liquid, such as activated sludge in a water treatment tank.

Although the present invention has been described in detail using specific embodiments, it will be apparent to those skilled in the art that various modifications and variations are possible without departing from the spirit and scope of the present invention.

This application is based on Japanese Patent Application No. 2018-16114 filed on Feb. 1, 2018, and the contents of which are incorporated herein by reference.

REFERENCE SIGN LIST

1 Main body member
2 First opening part

3 Second opening part
4 First flow channel
5 Second flow channel
6 Hollow part
7 First drive member
8 Second drive member
9 Imaging means
11 Coupling member
12 Second drive member (fixed state)
13 Coupling member having bellows structure

The invention claimed is:

1. A device for evaluating particles in a liquid, the device comprising:
- a main body comprising a first opening part and a second opening part facing each other, and a hollow region inside thereof;
- a first flow channel and a second flow channel connected to the main body and communicating with the hollow region;
- a first drive surface and a second drive surface provided in the hollow region so as to face each other and being slidable within the hollow region,
- wherein the first drive surface and/or the second drive surface is/are configured to be driven in a facing direction within the hollow region;
- a pump for introducing a liquid containing particles into the hollow region through the first flow channel; and
- a camera for capturing an image of particles within the hollow region through the first opening or the second opening,
- wherein when observing the first drive surface and the second drive surface from the facing direction, the first drive surface and the second drive surface include portions wider than the first flow channel and the second flow channel.

2. The device for evaluating particles in a liquid according to claim 1, comprising a coupling coupler attached to the main body and the first drive surface to maintain a liquid-tight state between the main body and the first drive surface.

3. The device for evaluating particles in a liquid according to claim 2, wherein the coupler has a bellows structure.

4. The device for evaluating particles in a liquid according to claim 1, wherein when observing the first drive surface and/or the second drive surface from the facing direction, the first drive surface and/or the second drive surface has substantially circular or polygonal shape.

5. A method for operating the device for evaluating particles in a liquid according to claim 1 comprising: driving the first drive surface and/or the second drive surface such that a width between the first drive surface and the second drive surface in the facing direction is 0.01 mm or more and less than 0.05 mm during observation, and is 0.5 mm or more at times other than the observation.

6. The method for operating the device for evaluating particles in a liquid according to claim 5, wherein the first drive surface and/or the second drive surface are/is driven in the facing direction at a speed of 5 mm/s or less.

* * * * *

UNITED STATES PATENT AND TRADEMARK OFFICE
CERTIFICATE OF CORRECTION

PATENT NO. : 11,181,465 B2
APPLICATION NO. : 16/966078
DATED : November 23, 2021
INVENTOR(S) : Shinji Okaya Page 1 of 1

It is certified that error appears in the above-identified patent and that said Letters Patent is hereby corrected as shown below:

In the Claims

In Column 10, Line 7, in Claim 2: "comprising a coupling coupler" should read --comprising a coupler--.

Signed and Sealed this
Twelfth Day of April, 2022

Drew Hirshfeld
*Performing the Functions and Duties of the
Under Secretary of Commerce for Intellectual Property and
Director of the United States Patent and Trademark Office*